(12) United States Patent
Miller et al.

(10) Patent No.: US 6,346,548 B1
(45) Date of Patent: Feb. 12, 2002

(54) COMPOSITIONS INCLUDING MODAFINIL FOR TREATMENT OF ATTENTION DEFICIT HYPERACTIVITY DISORDER AND MULTIPLE SCLEROSIS FATIGUE

(75) Inventors: Matthew S. Miller, Newtown, PA (US); Thomas E. Scammell, Wellesley, MA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 09/638,353

(22) Filed: Aug. 15, 2000

Related U.S. Application Data

(60) Provisional application No. 60/149,612, filed on Aug. 16, 1999.

(51) Int. Cl.⁷ .............................................. A61K 31/165
(52) U.S. Cl. ...................................................... 514/618
(58) Field of Search .......................................... 514/618

(56) References Cited

U.S. PATENT DOCUMENTS

| | | |
|---|---|---|
| 4,177,290 A | 12/1979 | Lafon |
| 4,927,855 A | 5/1990 | Lafon |
| 5,180,745 A | 1/1993 | Lafon |
| 5,618,845 A | 4/1997 | Grebow et al. |
| 5,719,168 A | 2/1998 | Laurent |

FOREIGN PATENT DOCUMENTS

| | | |
|---|---|---|
| WO | WO 99/25329 | 5/1999 |

OTHER PUBLICATIONS

Simon, P. et al., *Eur. Neuropsychopharm* 1995, 5, 509–514.
Ferraro, L et al., *Biol. Psychiatry* 1997, 42, 1181–1183.
Lin, J.S. et al., *Proc. Natl. Acad. Sci. USA* 1996, 93, 14128–14133.
Swanson et al., "Cognitive neuroscience of attention deficit hyperactivity disorder and hyperkinetic disorder," *Current Opinion in Neurobiology*, 1998, 8, 263–271.
Roelcke et al., "Reduced glucose metabolismin the frontal cortex and basal ganglia of multiple sclerosis patients with fatigue: A $^{18}$F–fluorodeoxyglucose positron emission tomography study," *Neurology*, 1997, 48, 1566–1571.

*Primary Examiner*—Rebecca Cook
(74) *Attorney, Agent, or Firm*—Robert T. Hrubiec; Eric K. Voelk

(57) ABSTRACT

Modafinil is effective in improving symptoms of attention deficit hyperactivity disorder and symptoms of multiple sclerosis fatigue. The administration of modafinil is also shown to activate the tuberomamillary neurons of the posterior hypothalamus, and thus exhibits activity in an area of the brain associated with normal wakefulness functions.

12 Claims, No Drawings

COMPOSITIONS INCLUDING MODAFINIL FOR TREATMENT OF ATTENTION DEFICIT HYPERACTIVITY DISORDER AND MULTIPLE SCLEROSIS FATIGUE

This application claims priority of Ser. No. 60/149,612 filed Aug. 16, 1999.

BACKGROUND OF THE INVENTION

1. Field of the Invention

The present invention is related to the fields of neuropharmacological agents, including agents that are useful in the treatment of attention deficit hyperactivity disorder and multiple sclerosis associated fatigue.

2. Description of Related Art

Attention-deficit/hyperactivity disorder (ADHD) is a chronic neuropsychiatric disorder in children that is characterized by developmentally inappropriate hyperactivity, impulsivity, and inattention. ADHD is estimated to affect 3%–5% of school-age children. Historically ADHD was thought not to continue beyond adolescence; however, current research suggests that ADHD persists into adulthood in 10% to 60% of childhood-onset cases. ADHD persistence is associated with a high incidence of academic and occupational dysfunction, as well as a high incidence of psychiatric comorbidity (e.g., conduct, major depressive, and anxiety disorders). It is estimated that approximately 1% to 3% of adults have symptoms of ADHD. Adults with ADHD have a pattern of demographic, psychosocial, psychiatric, and cognitive features that mirrors well-documented findings among children with the disorder. This further supports the validity of the diagnosis for adults. The core ADHD symptoms in adults include a frequent and persistent pattern of inattention/distractibility and/or hyperactivity-impulsivity. The most common symptoms exhibited in ADHD adults are marked inattention, poor concentration, easy distractibility, day dreaming, forgetfulness and a frequent shift in activities. ADHD adults also report marked impulsivity, intrusiveness, low frustration/stress tolerance, temper tantrums, irritability, and extreme impatience. Less commonly reported symptoms in adults include hyperactivity, which may be confined to fidgeting, or an inward feeling of jitteriness or restlessness. In addition to the core ADHD symptoms, adults with ADHD often exhibit associated clinical characteristics such as boredom, social inappropriateness, and chronic conflicts in social situations. These features may be responsible for the high incidence of: (1) separation and divorce and (2) poor academic performance and occupational achievement that exist despite adequate intellectual abilities. In addition, adults with ADHD have a high incidence of substance abuse disorders.

While the pathogenesis of ADHD remains unclear, alterations in the dopaminergic and noradrenergic functions appear to be the neurochemical basis for the disorder. Brain positron emission tomography in adults with ADHD have revealed alterations in glucose metabolism in areas of the cerebral cortex that are involved with attention and motor activity, like the frontal lobe. The most common treatment for both adult and pediatric ADHD is stimulants (e.g., dextroamphetamine, methylphenidate, and pemoline). Stimulants are thought to work by increasing the amount of dopamine available in the synapses of the neuron. The stimulants appear to do this in multiple cerebral anatomical locations. Other therapies that have been used include: antidepressants (e.g., tricyclic antidepressants such as imipramine and desipramine; novel antidepressants such as buproorion and venlafaxine), antihypertensives (e.g., clonidine and guanfacine), monoamine oxidase inhibitors ([MAO's], e.g., selegiline), amino acids (e.g., levodopa, phenylalanine, and L-tyrosine), and combined pharmacotherapies (e.g., concurrent use of a serotonin-selective reuptake inhibitor and a stimulant medication; or a stimulant and catelcholaminergic antidepressant regimen) (Bhandary et al., *Psychiatric Annals* 27:545–555, 1997; Wilens et al., *J. Clin. Psychopharmacol.* 15:270–279, 1995; Finkel, *The Neurologist* 3:31–44, 1997; Miller and Catellanos, *Pediatrics in Review* 19:373–384, 1998).

While stimulants are the most commonly used treatments, approximately 30%–50% of adults with ADHD do not respond positively to the stimulants, have unacceptable side effects or have concurrent depressive or anxiety disorders that stimulant medications may exacerbate or be ineffective in treating. The long-term adverse effects and their use in high-risk substance abuse subgroups of ADHD remain unstudied and are of concern; thus, there is still a need for nonstimulant pharmacotherapy for ADHD.

Another condition for which there is a long felt need for a non-stimulant pharmacological therapy is the fatigue associated with multiple sclerosis (MS). Multiple sclerosis is one of the most common disabling neurologic diseases of young adults in the United States, where an estimated 400,000 persons have the disease. Although MS can cause a variety of disabling neurological impairments such as blindness, paralysis, incoordination, and bowel or bladder dysfunction, a less apparent symptom that can also be severely disabling is fatigue. In one study involving 656 patients with MS, 78% complained of fatigue, 60% experienced it every day, and 22% suffered disruption of their daily activities (Freal et al., *Arch. Phys. Med. Rehabil.* 65:135, 1984). The National Multiple Sclerosis Society evaluated 839 patients who had only minor neurologic impairment despite having had MS for longer than 10 years, and fatigue was the most commonly reported symptom in this group of mildly affected patients (Jones, New York: National Multiple Sclerosis Society, Health Services Research Report, 1991). In another study 40% of MS patients listed fatigue as the most serious symptom of their disease (Murray, *Can. J. Neurol. Sci.* 12:251, 1985). Fatigue is reported to be the cause of at least temporary disability in up to 75% of patients with MS; and the British MS Society found fatigue to be the most important symptom leading to unemployment in this group (Rolak, *Curr. Neurol.* 9:109, 1989). In the United States, the prevalence of disability related to MS fatigue is underscored by its inclusion as a criterion for disability allowance under guidelines set forth by the Social Security Administration.

The mechanism of MS fatigue is poorly understood. It has been attributed to nerve conduction abnormalities within the central nervous system and increased energy demands caused by neurologic disability. Several characteristics of MS fatigue are interference with physical functioning and activities of daily living, aggravation by heat, and worsening at the end of the day (Krupp et al., *Arch. Neurol.* 45:435, 1988). Medications that are prescribed for the treatment of MS fatigue include amantadine, pemoline, and other stimulants. Amantadine has been demonstrated to benefit MS fatigue in 79% of patients in a double blind, randomized study, but its mechanism of beneficial action is not known (Krupp et al., Neurology 45:1956, 1995). Although amantadine has been demonstrated in a rigorous fashion to benefit MS fatigue, the benefit is partial for most patients and there are still significant numbers of patients who report no benefit. The same study failed to show a beneficial effect for pemoline, which is often used in the treatment of MS fatigue. There is a strong need, therefore, for a safe and effective treatment for this debilitating condition.

SUMMARY OF THE INVENTION

The present disclosure provides a novel use for modafinil in treatment of attention deficit hyperactivity disorder (ADHD) and in ameliorating the symptoms of fatigue due to multiple sclerosis (MS).

Studies forming the basis of the present disclosure demonstrate that, unexpectedly, administration of wake-promoting doses of modafinil to rats results in selective increases in activity of the tuberomamillary nucleus (TMN) of the posterior hypothalamus. Modafinil administration reduced the activity of the neurons in the ventrolateropreoptic area (VLPO) of the hypothalamus which are known to inhibit the activity during sleep of wake-promoting histaminergic neurons in the TMN. Activation of this histaminergic pathway by modafinil results in cortical activation and wakefulness. Thus, it appears that the physiologic basis for the wake-promoting actions of modafinil involves disinhibition of histaminergic neurons of the TMN by inhibitory actions on the VLPO. This represents the first pharmacologic agent known to produce wakefulness by selective activation of the TMN and was unexpected based on the previous publications in the field.

Based on these mechanistic studies, modafinil has a significantly different activity than the stimulants in common use for ADHD and MS fatigue. These are quite different drugs, as it is herein disclosed that modafinil promotes wakefulness by selective activation of hypothalamic nuclei involved in normal wakefulness, and in contrast, commonly used psychostimulants, such as amphetamines, act largely by enhancing dopaminergic input to the cortex and other brain regions by facilitating neurotransmission of dopaminergic neurons in the mesolimbic, tuberoinfundibular and nigrostriatal systems. Of these major dopaminergic pathways, the mesolimbic system originating in the ventral tegmentum may be most directly involved in cortical activation while the tuberoinfundibular and nigrostriatal systems are involved in pituitary and motor function, respectively. Simultaneous facilitation of these pathways by amphetamines results in the well-characterized cortical stimulation and hyperactivity associated with amphetamine administration. In contrast to the hypothalamic systems involved in normal wakefulness, facilitation of dopaminergic neurotransmission appears to induce a state of wakefulness that is abnormal in that it is associated with alterations in mood and perceptions of well-being as well as increases in motor activity.

Because of the surprising discovery of activation of the tuberomamillary neurons of the posterior hypothalamus by modafinil, as disclosed herein, novel uses for modafinil are revealed and such uses are an aspect of the present invention. For example, it is an aspect of the present invention that modafinil is a novel therapeutic agent that would provide important benefits for patients suffering from ADHD. Because modafinil activates the hypothalamus, and further because an inhibitory histaminergic neural pathway from the hypothalamus synapses on inhibitory gamma-aminobutyric acid (GABA) frontal lobe interneurons, the activation of the hypothalamus may contribute to subsequent pyramidal cell activation and provides a mechanism for the usefulness of modafinil in ADHD. In addition, activation of the TMN can also result in enhanced cortical action by direct histerminergic excitation. In other words, activation of the TMN neurons is excitory either directly or indirectly to the cortex.

Insufficient activity at the frontal cortex has been implicated in the etiology of ADHD (Castellanos, F. X., *Clinical Pediatrics*, 381–393 (1997); Swanson, J., et al., *Current Opinion in Neurobiology*, 8:263–271 (1998); Barkley, R. A., *Scientific American*, 66–71 (1998)).

An aspect of the present disclosure may be described therefore as a method of treating attention deficit hyperactivity disorder, where the treatment includes administering to a subject suffering from or susceptible to the development of attention deficit hyperactivity disorder a composition that includes a modafinil compound in an amount effective to improve or prevent symptoms of attention deficit hyperactivity isorder in said subject.

An additional aspect of the present disclosure is a method of treating fatigue associated with multiple sclerosis including administering to a subject suffering from multiple sclerosis fatigue a composition that contains a modafinil compound in an amount effective to improve or prevent symptoms of multiple sclerosis fatigue in the subject. As used herein "fatigue" includes loss of power, or capacity to respond to stimulation. As such, modafinil is shown herein to be effective as a treatment for alleviating tiredness, or sleepiness associated with multiple sclerosis and also as a method of promoting wakefulness in multiple sclerosis patients.

A further aspect of the disclosure is a method of treating a subject suffering from the symptoms of attention deficit hyperactivity disorder or multiple sclerosis fatigue that includes administering to the subject a pharmaceutical composition that includes a modafinil compound in an amount effective to stimulate activity in the tuberomamillary neurons of the brain of the subject.

Yet a further aspect of the disclosure is a pharmaceutical composition in unit dose form, for use in treating attention deficit hyperactivity disorder in a subject susceptible to the development of or suffering from attention deficit hyperactivity disorder, which includes an amount of a modafinil compound such that one or more unit doses thereof are effective to stabilize or improve the symptoms of attention deficit hyperactivity disorder in the subject upon periodic administration.

An aspect of the present disclosure is also a pharmaceutical composition in unit dose form, for use in treating fatigue in a multiple sclerosis patient, where the composition includes an amount of a modafinil compound such that one or more unit doses thereof are effective to stabilize or improve the symptoms of multiple sclerosis fatigue in the patient upon periodic administration.

As disclosed herein and as used in the compositions and methods of the present invention, a modafinil compound may include a racemic mixture, and may be in an acid form, such as a metabolic acid of modafinil or a benzhydrylsulfinylacetic acid, a sulfone form, a hydroxylated form, a conjugated form such as a modafinil compound conjugated to a protein, a polysaccharide, a glucuronide or a sulfate, or a polymorphic form, it may include compounds containing isosteric replacements of the phenyl groups of modafinil, and polymorphic species or analogs of modafinil, or derivatives of cogeners and prodrugs, particularly those preparations that stimulate activity in the TMN when administered to a mammal. In preferred embodiments, the modafinil compound is modafinil. Prodrugs are known in the art as compounds that are converted to the active agent (modafinil) in the body of a subject.

Compositions and methods as disclosed herein are preferably useful in the treatment of mammalian subjects, and more particularly in humans. Because MS and ADHD are known to afflict both adults and juveniles or children, the methods and compositions disclosed herein are directed to those population groups. While effective doses may be given in mg/day for human oral administration, it is understood that the dose, unless otherwise stated, may be directed to the treatment of a human adult and that a dose for a child is adjusted appropriately.

It is an object of the present invention to provide methods of treatment that include effective doses of a modafinil compound for the treatment of ADHD and MS fatigue, and that an effective amount is preferably from about 1 to about 400 mg per daily dose. It is known in the art, for example, that a dose of from about 200 mg/day to about 400 mg/day is an effective wake-promoting dose, and that such a dose is contemplated to be useful in treatment of ADHD and MS fatigue. It is also known that a dose of about 100 mg/day is at the lower threshold of wake-promoting doses, but that such a dose is contemplated to be useful for the treating ADHD and MS fatigue. Studies reported elsewhere have also shown beneficial activity of modafinil at sub-wakefulness-promoting doses, particularly in the improvement of cognitive function. As such, it is an aspect of the present disclosure that an effective amount of a modafinil compound for use in the methods disclosed herein may include from about 1 mg/day to about 400 mg/day, or from about 100 to about 400 mg per daily dose, or from about 200 to about 400 mg per daily dose, or even 200 mg per daily dose. It is also understood that doses within those ranges, but not explicitly stated, such as 30 mg, 50 mg, 75 mg, etc. are encompassed by the stated ranges, as are amounts slightly outside the stated range limits.

In the preferred embodiments, a composition including a modafinil compound is formulated for oral administration, and is more preferred to be formulated as a tablet for oral administration. The formulation of modafinil containing tablets is known in the art as described below, and such tablets may preferably contain various inert ingredients such as lactose, corn starch, magnesium silicate, croscarmellose sodium, povidone, magnesium stearate, or talc in any combination thereof.

An aspect of the present disclosure may also be described as a therapeutic package for dispensing to, or for use in dispensing to, a mammal being treated for attention deficit hyperactivity disorder or multiple sclerosis fatigue, where the package includes (1) one or more unit doses, each such unit dose containing an amount of a modafinil compound such that said one or more unit doses thereof are effective to stabilize or improve a symptom of attention deficit hyperactivity disorder or multiple sclerosis fatigue in the mammal upon periodic administration and the unit doses being administered periodically, and (2) a finished pharmaceutical container therefor, said container containing (a) said unit dose or unit doses and (b) labeling directing the use of the package in the treatment of said mammal. In preferred embodiments the package is adapted for oral administration.

Although the compositions and methods disclosed herein have been described in light of certain preferred embodiments, it is understood that the modafinil compounds described herein may be orally administered with an inert diluent or an assimilable edible carrier, for example. The compositions may also be enclosed in hard or soft shell gelatin capsule, compressed into tablets, or incorporated directly with the food of the diet. For oral therapeutic administration, the active compounds such as modafinil may be incorporated with excipients and used in the form of ingestible tablets, buccal tablets, troches, capsules, elixirs, suspensions, syrups, wafers, and the like, although tablets are the generally preferred method of administering modafinil. Such compositions and preparations should contain at least 0.1% of active compound. The percentage of the compositions and preparations may, of course, be varied and may conveniently be between about 2 to about 60% of the weight of the unit.

The tablets, troches, pills, capsules and the like may also contain any of the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring, for example. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

In certain embodiments, the disclosed compositions may be formulated to be administered by use of a skin patch, or transdermal delivery system. The administration of the modafinil compositions described herein transdermally may be accomplished by any of a number of systems known in the art. Examples of systems that may be adapted for use with the compositions described herein include those systems of transdermal administration described in U.S. Pat. No. 4,816,252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference.

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (See for examples, U.S. Pat. No. 4,906, 169).

The present invention further relates to a method for identifying a compound that stimulates activity in the TMN of the posterior hypothalamus. This method involves the use of standard screening techniques applied to the novel discovery as set out hereinabove. Accordingly, there is provided by the present invention compounds identified by this method and uses therefor as drugs wherein stimulation in the TMN of the posterior hypothalamus will have a salutary effect on the wellbeing of the animal or patient being treated.

DETAILED DESCRIPTION

Modafinil is an agent with activity in the central nervous system, and has been developed as a treatment for excessive daytime sleepiness associated with narcolepsy. The primary pharmacological activity of modafinil, like amphetaminelike agents, is to promote wakefulness. Modafinil promotes wakefulness in rats (Touret, et al., *Neuroscience Letters*, 189:43–46 (1995); Edgar and Seidel, *J. Pharmacol. Exp. Ther.*, 283:757–69 (1997)), cats (Lin et al., *Brain Research*, 591:319–326 (1992)), canines (Shelton et al, *Sleep* 18(10):817–826, (1995)) and non-human primates (DS-93-023, pp 180–181; Hernant et al., *Psychopharmacology*, 103:28–32 (1991)), as well as in models mimicking clinical situations, such as sleep apnea (English bulldog sleep disordered breathing model) (Panckeri et al, 1996) and narcolepsy (narcoleptic canine) (Shelton et al., *Sleep* 18(10):817–826, (1995)). Modafinil has also been demonstrated to be a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas of central origin (U.S. Pat. No. 5,612,378). U.S. Pat. No. 5,618,845 describes modafinil preparations of a defined particle size less than about 200 microns that is more potent and safer than preparations containing a substantial proportion of larger particles.

Various neuroanatomical pathways have been investigated for their role in inducing and maintaining wakefulness, and some of the work has pointed to the potential role of the tuberomamillary nucleus (TMN) (Sherrin et al., *Science* 271:216–219, 1996). A study by Lin et al., (Proceedings of the National Academy of Science, USA 93:14128–14133, 1996) demonstrated selective activation of the anterior hypothalamus by modafinil, and the authors of that study also demonstrated that administration of modafinil to cats at a wake-promoting dose failed to cause activation of the TMN of the posterior hypothalamus. A similar study of wake-promoting doses of modafinil administered to rats (Engber et al., *Neuroscience*, 87:905–911 (1998)) also demonstrated that modafinil-induced wakefulness was not associated with activation of the TMN. Thus, while activation of the TMN has been implicated in normal wakefulness, the studies of these researchers has clearly taught that TMN activation was not involved in modafinil-induced wakefulness.

The present invention arises in part from the discovery that modafinil, when administered at wakefulness-promoting doses, does result in a stimulation of activity in the TMN of the posterior hypothalamus. Modafinil administration in rats reduced the activity of the neurons in the ventrolateropreoptic area (VLPO) of the hypothalamus, which are known to inhibit the activity of wake-promoting histaminergic neurons in the TMN during sleep. Activation of this histaminergic pathway by modafinil results in cortical activation and wakefulness. Thus, it appears that the physiologic basis for the wake-promoting actions of modafinil involves disinhibition of histaminergic neurons of the TMN by inhibitory actions on the VLPO. This represents the first pharmacologic agent known to produce wakefulness by activation of the TMN. Furthermore, because modafinil activates the hypothalamus, and because an inhibitory histaminergic neural pathway from the hypothalamus synapses on inhibitory gamma-aminobutyric acid (GABA) frontal lobe interneurons, the present inventors contemplate that the activation of the hypothalamus contributes to subsequent pyramidal cell activation and provides a mechanism for the usefulness of modafinil in ADHD, and in MS fatigue (Swanson, J., et al., *Current Opinion in Neurobiology*, 8:263–271 (1998); Roelke, U., et al., *Neurobiology*, 48:1566–1571 (1997)).

Prior to any invention disclosed or claimed herein, modafinil was known in the art in the form of a therapeutic package, marketed under the name Provigil®. Provigil® is a pharmaceutical product manufactured by Cephalon, Inc. of West Chester, Pa. and is also marketed by Cephalon, Inc. Provigil® is supplied as tablets containing 100 mg or 200 mg modafinil. In commercial use, modafinil-containing therapeutic packages in the prior art were labeled and otherwise indicated for use in narcolepsy patients.

Accordingly, known in the prior art were therapeutic packages providing one or more unit doses of modafinil as an active ingredient thereof, supplied in a finished pharmaceutical container that contain said unit doses, and further contained or comprised labeling directing the use of said package in the treatment of a human disease or condition as described above. In the provided literature accompanying a pharmaceutical container are instructions that the daily dosage of modafinil is 200 mg/day given as a single dose in the morning. Although 400 mg/day was well tolerated in clinical trials, 200 mg/day is the optimum wakefulness promoting dose in adult humans.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLES

The invention is further illustrated by the following examples. The examples are provided for illustration purposes only, and they are not to be construed as limiting the scope or content of the invention.

Experimental Design: In the following examples, rats were sacrificed two hours following treatment, and the brains were analyzed using immunohistochemistry for Fos. In Examples 1 and 2, rats were instrumented for electroencephalogram (EEG) and electromyogram (EMG) recordings. To avoid the stress of handling during administration of modafinil or vehicle, chronic catheters were placed in the peritoneal cavity for administration of modafinil or vehicle.

Animals and Recording Environment: 65, male, Sprague-Dawley rats (Harlan) weighing 270–330 g were housed individually in a pathogen-free barrier facility in a room maintained at 21.5–22.5° C. with lights on at 7 AM and off at 7 PM. Rats had food and water available ad lib. At least 3 days before each experiment, rats were placed into a light-tight, sound-attenuated recording chamber (Biocube) in an isolated room. Light intensity was 100–150 lux at midlevel inside each cage. The Institutional Animal Care and Use Committees of Beth Israel Deaconess Medical Center and Harvard Medical School approved all procedures.

Animal Surgery: Under chloral hydrate anesthesia (350 mg/kg ip), the rats of Examples 1 and 2 were surgically implanted with four EEG screws (AP: +3, −4; RL: +2,−2 from bregma) lightly contacting the dura and two EMG wires (Plastics One, Roanoke, Va.) below the nuchal muscles. The leads were connected to a six channel connector (Plastics One) which was affixed to the skull with dental acrylic. A telemetric temperature transmitter (TA10TA-F40, Data Sciences International, St. Paul, Minn.) was placed in the peritoneal cavity of all but 5 rats. To administer drugs without handling the rats, an 80 cm silastic catheter (1 mm I.D., Baxter Scientific Products) was inserted into the peritoneal cavity, subcutaneously tunneled to the scalp, cemented in place with dental acrylic, and protected externally by a spring. This intraperitoneal catheter was filled with heparinized, pyrogen-free saline and flushed weekly and 3 days prior to the experiment. Animals recovered at least 14 days and then acclimated to recording cables for three days prior to the start of physiological recordings.

Drug Administration: Modafinil (lot #PA 008; Cephalon, Inc., West Chester, Pa.) was suspended in a solution of 0.25% methylcellulose (pH=7.4, Dow Chemical Inc., Midland, Mich.) in 0.9% pyrogen-free saline. The drug was administered in a volume of 2.0 ml/kg at doses of 150 mg/kg. Control animals received an equal volume of methylcellulose vehicle. Catheters were then flushed with 1 ml 0.9% saline to assure delivery of drug into the peritoneal cavity. A red flashlight was used to aid injections performed in the dark.

Histology and Immunohistochemistry: Two hours following drug injections, animals were deeply anesthetized with chloral hydrate (600 mg/kg ip) and transcardially perfused with 100 ml 0.9% saline followed by 500 ml of phosphate buffered 10% formalin, pH 7.0 (Sigma). Brains were removed, postfixed for 4 hours in formalin, and then allowed to equilibrate in 20% sucrose in 0.1 M phosphate buffered saline (PBS), with 0.02% sodium azide (Sigma) at 4° C. Brains were sectioned (1:5 series, 30 $\mu$m) on a freezing microtome and stored in PBS-azide at 4° C. One series from each brain was stained for Fos using previously described methods (Elmquist et al., 1996). Briefly, sections were incubated for 48 hours at 4° C. in anti-Fos rabbit polyclonal antiserum (Ab-5, Oncogene Research Products, 1:100,000 dilution), 3% donkey serum (Jackson ImmunoResearch), and PBS-azide with 0.25% Triton X-100 (PBT-Az). Tissue was then rinsed in PBS, incubated in biotinylated donkey anti-rabbit IgG (1:1,000, Jackson ImmunoResearch) for 1 hour at room temperature, incubated with peroxidase-conjugated avidin biotin complex (ABC, Vector) for 1 hour, followed by 0.05% diaminobenzidine tetrahydrochloride (DAB) and 0.01% $H_2O_2$ with 1% $NiSO_4$ and 0.5% $CoCl_2$, to produce a black reaction product in cell nuclei.

Cell Counts. The pattern of Fos-immunoreactivity was examined for the selected brain regions. To quantify these differences, Fos-IR neurons were counted in regions with possible modafinil-induced Fos by an examiner blinded to experimental conditions. For all nuclei, bilateral counts were taken on three consecutive sections, 120 $\mu$m apart, that contained the largest nuclear areas, and these 6 counts were averaged. In Example 1, Fos-IR nuclei were counted in regions implicated in behavioral state control: the ventrolateral preoptic area (VLPO), TMN, ventral tegmental area (VTA) and anterior cingulate cortex.

Statistical Analysis. Mann-Whitney rank-sum tests with a Bonferroni correction were used to compare Fos-IR cell counts; p was considered significant if <0.05.

Example 1

To determine the pattern of neuronal activation induced by modafinil, we administered modafinil (150 mg/kg) or vehicle at midnight, the normal wake period. The data is shown below in Table 1.

TABLE 1

Cell counts for rats treated with modafinil or vehicle at midnight. Values are means ± standard errors. Bold values are statistically significant from vehicle by a post-hoc Scheffe test

|  | Vehicle | Modafinil 50 mg/kg | Kruskal-Wallis p value |
|---|---|---|---|
| n | 6 | 6 | |
| Cingulate cortex | 52 ± 13 | 191 ± 38 | 0.008 |
| TMN | 13 ± 7 | 46 ± 4 | 0.005 |
| VTA | 8 ± 2 | 12 ± 3 | NS |

Following administration of modafinil (150 mg/kg), the TMN had four times as many Fos-IR neurons as seen in the controls (Table 1). Neurons of the VLPO are active during sleep (Sherin et al., Science 271:216–9. (1996); Alam et al., Annual Meeting of the Society for Neuroscience, Washington, D.C. 1996), and as all animals were mainly awake, it was not surprising that Fos-IR VLPO neurons were uncommon in all rats. Modafinil-treated rats had more Fos immunoreactivity in the cortex than the controls. This Fos induction was evident across much of the cortex, but was often more pronounced in cingulate and pyriform cortex with moderate amounts in frontal and parietal cortex, Example 2

In Example 2, modafinil (150 mg/kg) was administered at noon, the normal sleep period. The data is shown below in Table 2.

TABLE 2

Cell counts for rats treated with modafinil or vehicle at noon under LD or DD conditions. Bold values are statistically different than vehicle using a post-hoc Scheffe test

|  | Vehicle | Modafinil 150 mg/kg | Mann-Whitney p value |
|---|---|---|---|
| n | 6 | 7 | |
| VLPO | 52 ± 7 | 26 ± 3 | 0.007 |
| TMN | 8 ± 4 | 43 ± 5 | 0.003 |

In animals maintained on a normal LD cycle, administration of modafinil (150 mg/kg) at noon markedly increased number of Fos-IR neurons in the TMN, with decreases in the VLPO. Modafinil treatment also increased expression of Fos in frontal and cingulate cortex.

What is claimed is:

1. A method of treating attention deficit hyperactivity disorder comprising administering to a subject suffering from or susceptible to the development of attention deficit hyperactivity disorder a composition comprising a modafinil compound in an amount effective to improve or prevent symptoms of attention deficit hyperactivity disorder in said subject.

2. A method of treating the symptoms of attention deficit hyperactivity disorder in a subject in need thereof comprising administering to said subject a pharmaceutical composition comprising a modafinil compound in an amount effective to stimulate activity in the tuberomamillary neurons of the brain of said subject.

3. The method of claims 1 or 2, wherein said modafinil compound is modafinil.

4. The method of claims 1 or 2, wherein said subject is an adult human.

5. The method of claims 1 or 2, wherein said subject is a human child.

6. The method of claims 1 or 2, wherein said effective amount is from about 1 to about 400 mg per daily dose.

7. The method of claims 1 or 2, wherein said effective amount is from about 100 to about 400 mg per daily dose.

8. The method of claims 1 or 2, wherein said effective amount is from about 200 to about 400 mg per daily dose.

9. The method of claims 1 or 2, wherein said effective amount is about 200 mg per daily dose.

10. The method of claims 1 or 2, wherein said composition comprising a modafinil compound is formulated for oral administration.

11. The method of claims 1 or 2, wherein said composition comprising a modafinil compound is formulated as a tablet.

12. The method of claim 11, wherein said tablet further comprises one or more ingredients selected from the group consisting of lactose, corn starch, magnesium silicate, croscarmellose sodium, povidone, magnesium stearate, and talc.

* * * * *